United States Patent [19]

Fozard et al.

[11] Patent Number: 4,563,465
[45] Date of Patent: Jan. 7, 1986

[54] TREATMENT OF MIGRAINE WITH SUBSTITUTED TROPYL BENZOATE DERIVATIVES

[75] Inventors: John R. Fozard, Strasbourg-Elsau; Maurice W. Gittos, Plobsheim, both of France

[73] Assignee: Merrell Dow Pharmaceuticals Inc., Cincinnati, Ohio

[21] Appl. No.: 681,984

[22] Filed: Dec. 13, 1984

Related U.S. Application Data

[63] Continuation-in-part of Ser. No. 386,562, Jun. 9, 1982, abandoned.

[30] Foreign Application Priority Data

Jun. 13, 1981 [GB] United Kingdom ............... 8118249

[51] Int. Cl.[4] ............................................. A61K 31/44
[52] U.S. Cl. ..................................................... 514/304
[58] Field of Search .................... 424/265; 546/129; 514/304

[56] References Cited

U.S. PATENT DOCUMENTS 3,170,927  2/1965  Nádor et al. ........................ 26/292

OTHER PUBLICATIONS

Fozard, Adv. in Neurology, 33—295-307 (1982).
Fozard et al., European Journal of Pharmacology, 59 195-209 (1979).
Chem. Abst. 28-5596[9](1934), 30-1871[6](1934), 34-7009[7](1940), 59-5665g(1963), 67-53953 & 78-119197, 39-1926[8](1945), 63-16951G.
Chem. Abst. 85 (1976)—87108t.

Primary Examiner—Stanley J. Friedman
Attorney, Agent, or Firm—William J. Stein; Raymond A. McDonald

[57] ABSTRACT

Migraine is treated with a tropyl benzoate derivative of the following general formula:

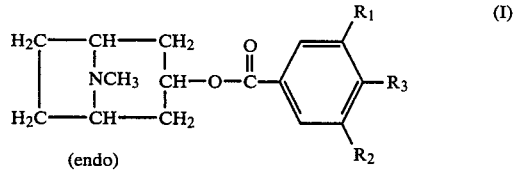

(endo)

wherein:
$R_1$ represents $C_1$–$C_4$ alkyl, $C_1$–$C_4$ alkoxy or halogen;
$R_2$ represents hydrogen, $C_1$–$C_4$ alkyl, $C_1$–$C_4$ alkoxy or halogen; and
$R_3$ represents hydrogen, $C_1$–$C_4$ alkyl, $C_1$–$C_4$ alkoxy or halogen, provided that $R_3$ is hydrogen when $R_2$ is hydrogen, or a pharmaceutically acceptable salt thereof.

Additionally, some novel tropyl benzoate derivatives are disclosed.

10 Claims, No Drawings

TREATMENT OF MIGRAINE WITH SUBSTITUTED TROPYL BENZOATE DERIVATIVES

This application is a continuation-in-part application of Ser. No. 386,562, filed June 9, 1982, now abandoned.

FIELD OF THE INVENTION

This invention relates to the treatment of migraine with certain tropyl benzoate derivatives and provides pharmaceutical compositions comprising said compounds for use in the treatment of migraine. Additionally, certain novel compounds per se are described.

BACKGROUND OF THE INVENTION

Acute attacks of migraine are usually treated with a peripheral vasoconstrictor, such as ergotamine, which may be co-administered with caffeine, and dihydroergotamine; an antipyretic analgesic, such as acetylsalicylic acid or p-acetylaminophenol; and/or an antiemetic such as cyclizine, metoclopramide and thiethylperazine. It has also been reported (J. B. Hughes, Med. J. Aust. 2, No. 17, 580, 1977) that immediate relief of acute migraine attack can be obtained by the slow intravenous injection of metoclopramide (10 mg).

It is believed that 5-hydroxytryptamine or serotonin (5-HT) is the naturally occurring substance most likely to play a role in the pathophysiology of migraine. Increased amounts of 5-HT and its metabolite 5-hydroxyindoleacetic acid are excreted in the urine during most attacks. Further, plasma and platelet 5-HT concentrations rapidly fall at the onset of an attack and remain low while the headache persists. Moreover, attacks of migraine have been clearly associated with periods of thrombocytopaenia in certain patients. It has been proposed that compounds which block the activity of 5-HT would be of use in the treatment of migraine (J. R. Fozard, International Headache Congress 1980, reported in Advances in Neurology, Vol. 33, Raven Press, New York, 1982).

The known migraine prophylactic drugs, methysergide, propanolol, amitriptyline, and chlorpromazine have widely different pharmacological activities but are all 5-HT D-receptor antagonists at the doses used clinically for the treatment of migraine. Metoclopramide is a potent 5-HT M-receptor antagonist and it has been proposed (J. R. Fozard supra) that a blockade of the M-receptor present on afferent sensory neurones affords symptomatic relief in an acute migraine attack.

It is an object of the present invention to provide compounds which are more potent and selective 5-HT M-receptor antagonists than metoclopramide and which can be useful for the treatment of migraine.

The potency as 5-HT M-receptor antagonists of (−) cocaine and some related compounds has been reported (J. R. Fozard et al, Eur. J. Pharmacol, 59, 1979, 195–210). However, with the exceptions of nor(−)cocaine and benzoyltropine, none are as potent as metoclopramide. The $pA_2$ values reported for nor(−) cocaine and benzoyltropine are 7.7 and 7.12 respectively, while the $pA_2$ 5-HT value determined for metoclopramide by the same procedure is 7.2 (J. R. Fozard et al, Eur. J. Pharmacol., 49, 1978, 109–112).

Surprisingly, it has been found that di- or tri-substitution of benzoyltropine by alkyl, alkoxy or halogen in the 3,4 or 3,4 or 3,4,5 positions of the benzene ring substantially enhances the potency of benzoyltropine as a 5-HT M-receptor antagonist.

The following tropyl benzoate derivatives are known compounds.

| KNOWN TROPYLBENZOATES OF FORMULA I | | | |
|---|---|---|---|
| $R_1$ | $R_2$ | $R_3$ | Reference |
| $OCH_3$ | H | H | C.A. 59, 5665 |
| $OCH_3$ | $OCH_3$ | $OCH_3$ | |
| $OCH_3$ | $OCH_3$ | $OC_4H_9$ | C.A. 67, 53963 |
| Cl | H | H | C.A. 78, 119197 |
| Cl | Cl | H | |
| $OCH_3$ | H | $OCH_3$ | C.A. 28, 5596[9] |
| $CH_3$ | $CH_3$ | H | UK Patent 1,012,622 |

Some of these known tropyl benzoate derivatives and certain known positional isomers thereof have been reported to have pharmacological activity, specifically local anesthetic, central nervous system stimulant, cholinolytic and/or spasmolytic activity. However no pharmacological activity indicating their use for the treatment of migraine has been reported.

The compounds of formula (I) below can be effectively administered in the treatment of migraine at dose levels well below those at which pharmacological activity has previously been reported for any of the said known compounds or their known isomers.

SUMMARY OF THE INVENTION

According to a first aspect of the invention, there are provided for use in the treatment of migraine and other vascular headaches, tropyl benzoate derivatives having the following general formula:

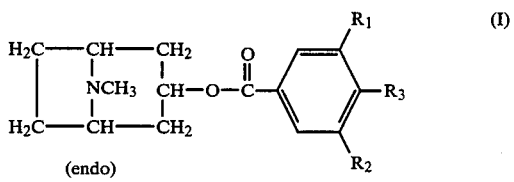

(endo)

wherein:

$R_1$ represents $C_1$–$C_4$ alkyl, $C_1$–$C_4$ alkoxy or halogen;

$R_2$ represents hydrogen, $C_1$–$C_4$ alkyl, $C_1$–$C_4$ alkoxy or halogen; and $R_3$ represents hydrogen, $C_1$–$C_4$ alkyl, $C_1$–$C_4$ alkoxy or halogen, provided that $R_3$ is hydrogen when $R_2$ is hydrogen, or a pharmaceutically acceptable salt thereof.

The use of the compounds of formula (I) in the treatment of migraine comprises administering an effective migraine relieving amount of the active ingredient to a patient in need thereof. The amount of active ingredient employed usually will be in the range of from 0.01 mg/kg to 10 mg/kg, and more particularly in the range of 0.03 mg/kg to 3.0 mg/kg. It is also contemplated that the compounds of formula (I) can be employed in the prophylaxis of migraine by administering to a patient at risk of migraine an effective migraine prophylactic amount of the active ingredient.

According to a second aspect of this invention there are provided a limited group of pharmaceutical compositions in unit does form for the effective relief of migraine which comprises compounds of general formula (II) below in admixture or otherwise associated with a pharmaceutically acceptable diluent or carrier.

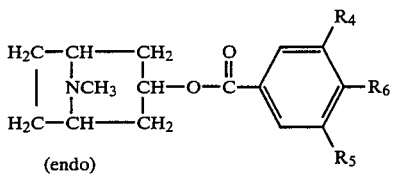

wherein $R_4$ and $R_5$ are chlorine or methyl, $R_6$ is hydrogen, or a pharmaceutically acceptable salt thereof. In general such compositions will contain from 50 mg to 125 mg of active ingredient per unit dose. Preferably, a unit dose contains from 75 mg to 100 mg of the active ingredient.

According to a third aspect of this invention, there are provided novel compounds per se as shown in general formula (III) below which are useful as antimigraine agents.

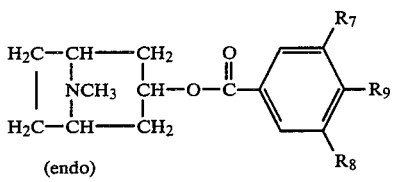

wherein
$R_7$ i $C_1$-$C_4$ alkyl, $C_1$-$C_4$ alkoxy or hologen;
$R_8$ is $C_1$-$C_4$ alkyl or $C_1$-$C_4$ alkoxy;
$R_9$ is hydrogen or $C_1$-$C_4$ alkyl, with the proviso that when $R_7$ is alkyl, then $R_9$ must also be alkyl; or a pharmaceutically acceptable salt thereof.

DETAILED DESCRIPTION OF THE INVENTION

The compounds of general formula (I) have the benzoyloxy moiety substituted in that $R_1$ represents $C_1$-$C_4$ alkyl, $C_1$-$C_4$ alkoxy or halogen; $R_2$ can represent $C_1$-$C_4$ alkyl, $C_1$-$C_4$ alkoxy or halogen; and $R_3$ is hydrogen except when $R_2$ is other than hydrogen, in which case $R_3$ can represent $C_1$-$C_4$ alkoxy or halogen.

Examples of $C_1$-$C_4$ alkyl groups which can be represented by $R_2$, $R_3$ and $R_4$ are methyl, ethyl, n-propyl, n-butoxy and iso-propyl with methyl and ethyl being the preferred groups.

Examples of $C_1$-$C_4$ alkoxy groups which can be represented by $R_2$, $R_3$ and $R_4$ are methoxy, ethoxy, n-propoxy, n-butoxy and iso-propoxy, with ethoxy and especially methoxy being the preferred groups.

The halogens which can be represented by $R_2$, $R_3$ and $R_4$ are bromine, chlorine, fluorine and iodine with chlorine being the preferred halogen.

A preferred class of compounds are those of formula (I) in which $R_1$ represents methyl, methoxy or chlorine, $R_2$ represents hydrogen, and $R_3$ represents hydrogen.

Another preferred class of compounds are those of formula (I) in which $R_1$ and $R_2$ are the same and each represents methyl, methoxy or chlorine, and $R_3$ represents hydrogen.

Yet another preferred class of compounds are those of formula (I) in which $R_1$, $R_2$ and $R_3$ are all the same and each represents methyl, methoxy or chlorine.

One particularly preferred embodiment of the invention includes those compounds of formula (I) in which (a) $R_1$ represents methoxy and $R_2$ and $R_3$ represent hydrogen, (b) $R_1$ and $R_2$ both represent methoxy and $R_3$ represents hydrogen, or (c) $R_1$, $R_2$ and $R_3$ each represents methoxy. Such compounds include:
tropyl 3-methoxybenzoate;
tropyl 3,5-dimethoxybenzoate; and
tropyl 3,4,5-trimethoxybenzoate.
The di- and tri-methoxy compounds are preferred over the monomethoxy compound.

Another particularly preferred embodiment of the invention includes those compounds of formula (I) in which (a) $R_1$ represents chlorine and $R_2$ and $R_3$ represent hydrogen, (b) $R_1$ and $R_2$ both represent chlorine and $R_3$ represents hydrogen, or (c) $R_1$, $R_2$ and $R_3$ each represent chlorine. Such compounds include:
tropyl 3-chlorobenzoate;
tropyl 3,5-dichlorobenzoate; and
tropyl 3,4,5-trichlorobenzoate.
The dichloro compound is preferred over the mono- or tri-chloro compounds.

In addition to the preferred methoxy and chloro compounds specified above, the following compounds illustrate the scope of the compounds of formula (I):
tropyl 3,5-dibromobenzoate;
tropyl 3,5-diiodobenzoate;
tropyl 3,5-difluorobenzoate;
tropyl 3,5-diethoxybenzoate;
tropyl 3-methoxy-5-chlorobenzoate;
tropyl 31 -methylbenzoate;
tropyl 3,5-dimethylbenzoate;
tropyl 3,4,5-trimethylbenzoate;
tropyl 3,5-diethylbenzoate;
tropyl 3,5-di-n-butoxybenzoate.

The compounds of formula (I) block the M-receptors for 5-hydroxytryptamine (5-HT) on afferent sensory neurones, certain of which subserve the transmission of pain. As explained above, the blocking of such M-receptors is believed to be a mechanism whereby the symptoms of migraine can be relieved. Accordingly, the compounds of formula (I) are useful in the treatment of migraine when administered in amounts sufficient to effectively block the said M-receptors.

The activity of the compounds against 5-HT can be assessed by determining their $pA_2$ values in the isolated rabbit heart as described by J. R. Fozard et al, Eur. J. Pharmacol., 59, 195–210 (1979). In the method described, the molar concentration of antagonist which reduces the effects of twice the $ED_{50}$ of 5-HT to that of the $ED_{50}$ in the absence of antagonist is determined. The $pA_2$ value is the negative logarithm of said molar concentrations. In general terms, the higher the $pA_2$ value the more potent is the compound.

The $pA_2$ values of some representative compounds of formula (I) are given in the following Table II:

TABLE II

| Compound | $pA_2$ 5-HT |
| --- | --- |
| tropyl 3-methylbenzoate | 8.2 |
| tropyl 3,5-dimethoxybenzoate | 8.4 |
| tropyl 3,4,5-trimethoxybenzoate | 8.5 |
| tropyl 3-chlorobenzoate | 8.6 |
| tropyl 3,5-dimethylbenzoate | 9.0 |
| tropyl 3,5-dichlorobenzoate | 9.3 |

The $pA_2$ values of some closely structurally related compounds to those of the present invention are given in the following Table III for comparative purposes.

TABLE III

| Compound | pA$_2$ 5-HT |
| --- | --- |
| tropyl 4-chlorobenzoate | 7.0 |
| tropyl 3,4-dimethoxybenzoate | 7.2 |
| tropylbenzoate | 7.2 |
| tropyl 4-methylbenzoate | 7.8 |
| nortropyl 3,5-dichlorobenzoate | 7.8 |

It will be noted from Tables II and III that the compounds of formula (I) show in this test a potency as 5-HT M-receptor antagonists of at least an order of magnitude greater than that for tropylbenzoate.

The activity of these compounds against 5-HT can be assessed in vivo by measurement of the effect of the compound on the Von Bezold-Jarisch Reflex induced by 5-HT injected intravenously into the rat (A.S. Paintal, Physiol. Rev. 53, 159–227, 1973). The transient cardiac slowing arises from an increased afferent vagus activity arising from stimulation by 5-HT of sensory afferent fibres in and around the heart (see Example 3).

The compounds of formula (I) are highly selective in their action against 5-HT M-receptor. Their potency against other 5-HT receptors and other spasmogens, in particular oxytocin, acetylcholine, histamine and calcium, appears to be at least two orders of magnitude lower than that against 5-HT M-receptors (see Example 4). Accordingly, their use in the treatment of migraine should be without side effects.

The compounds of formula (I) can be administered to the patient in various manners to achieve the desired effect. The compounds can be administered alone or in the form of pharmaceutical preparations, the patient being treated either orally or parenterally, for example, subcutaneously or intravenously. The amount of compound administered will vary and can be any effective migraine-relieving amount. Depending upon the patient and the mode of administration, the quantity of compound administered may vary over a wide range to provide from about 0.01 mg/kg to about 10 mg/kg, usually 0.03 to 3.0 mg/kg, of body weight of the patient per dose. Unit doses of these compounds can contain, for example, from about 50 mg to 125 mg of the active ingredient. Preferably, 75 mg or 100 mg of the active ingredient is administered to the patient per unit dose once a day and no more than two times daily.

It will be appreciated that the dosage levels for the compounds of formula (III) referred to above are substantially less than those required for medical treatment based on any known pharmacological activity for any of the known compounds of formula (I). In the particular case of tropyl 3,5-dichlorobenzoate, for example, in vitro data (see Table VI) indicate that the dose levels for treating migraine are between 4,500 and at least 62,00 times less than the dose required to produce a spasmolytic effect as suggested by the prior art teachings. Accordingly, those pharmaceutical compositions which can be inferred from the prior art teachings would not be effective or useful in the treatment of migraine.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the pharmaceutical composition aspects of this invention, there are provided pharmaceutical formulations in which form the active compounds of the invention will normally be utilized. Such formulations are prepared in a manner well known in the pharmaceutical art and usually comprise at least one active compound of the invention in admixture or otherwise in association with a pharmaceutically acceptable carrier or diluent therefor. For the preparation of these formulations the active ingredient will usually be mixed with a carrier, or diluted by a diluent, or enclosed or encapsulated in a capsule, sachet, cachet, paper or other container. The carrier or diluent may be solid, semi-solid or a liquid material which serves as a vehicle, excipient or medium for the active ingredient. Suitable carriers or diluents are well known to those skilled in the art.

The formulations of the invention may be adapted for enteral or parenteral use and may be administered to the patient in the form of tablets, capsules, suppositories, solutions, suspensions and the like. In the specific examples included hereinabelow illustrative examples of suitable pharmaceutical formulations are described.

The tropylbenzoate derivatives of formula (I) can be used in migraine therapy in combination with other antimigraine drugs having different modes of action. Such drugs include those used prophylactically, such as barbiturates, diazepam, chlorpromazine, amitriptyline, propanolol, methysergide, pizotifen, cyproheptadine, dihydroegotamine, and clonidine, as well as those used in the acute attack, such as vasoconstrictor agents, e.g., ergotamine and dihydroergotamine, analgestic/anti-inflammatory agents, e.g., aspirin, paracetamol and indomethacin, or anti-nauseants, e.g., cyclizine, metoclopramide, and triethylperazine (J. R. Fozard, J. Pharm. Pharmacol., 27, 297–321 (1975); J. R. Saper, J. Amer. Med. Assoc. 239, 480–484 (1978); J. R. Fozard, supra). As an example, compounds of general formula (I) would be beneficial in combination with aspirin 300–1200 mg or methysergide 2–6 mg given daily.

As mentioned above, certain of the compounds of formula (I) are known compounds and hence their preparation or, in the case of naturally occurring compounds, their isolation is described in the literature. In general, the compounds of general formula (I) can be prepared in a manner known per se by the reaction of tropine with an acid halide having the following general formula (IV):

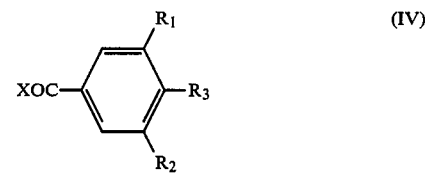

wherein

R$_1$, R$_2$ and R$_3$ are as defined in connection with formula (I), and

X represents halogen, especially chlorine.

The reaction can be carried out in the absence of a solvent by heating at, for example, a temperature in the range 140° to 160° C. the acid halide with a hydrohalide salt of tropine while stirring. Hydrogen halide is evolved and the mixture first becomes liquid but subsequently becomes solid. Heating is continued for about 15 minutes after solidification and the mixture is cooled and added to water. The product is the hydrohalide of the compound of formula (I). The corresponding free base can be obtained by the addition of an aqueous base to render the aqueous solution containing the product alkaline. A base such as sodium or potassium carbonate is generally employed which does not hydrolyse the benzoyl ester. The free base can be subsequently extracted with a suitable organic solvent such as, for example, diethyl ether, ethyl acetate and methylene chloride. The organic solution is subsequently evaporated and the residue recrystallized from, for example, aqueous methanol.

As previously mentioned, the compounds of formula (I) can be used in the form of their pharmaceutically acceptable acid addition salts.

The pharmaceutically acceptable acid addition salts can be non-toxic addition salts with suitable acids, such as those with inorganic acids, for example hydrochloric, hydrobromic, nitric, sulfuric or phosphoric acids, or with organic acids, such as organic carboxylic acids, for example, glycolic, maleic, hydroxymaleic, malic, tartaric, citric, salicylic, o-acetyloxy-benzoic, nicotinic or isonicotinic, or organic sulphonic acids, for example methane sulphonic, ethane sulphonic, 2-hydroxyethane sulphonic, toluene-p-sulphonic, or naphthalene-2-sulphonic acids.

Apart from pharmaceutically acceptable acid addition salts, other acid addition salts such as for example, those with picric or oxalic acid, may serve as intermediates in the purification of the compounds or in the preparation of other, pharmaceutically acceptable, acid addition salts or the preparation of salts which may be useful for the identification or characterization of the parent free bases.

An acid addition salt may be converted into the free compound according to known methods, for example, by treating it with a base, such as with an alkali or alkaline earth metal hydroxide, for example, lithium hydroxide, sodium hydroxide, potassium hydroxide or calcium hydroxide; with an alkali metal or an alkaline earth metal carbonate or hydrogen carbonate, for example, sodium, potassium or calcium carbonate or hydrogen carbonate; with trialkylamine; or with an anion exchange resin.

An acid addition salt may also be converted into another acid addition salt according to known methods. For example, a salt with an inorganic acid may be treated with a metal salt, for example a sodium, barium or silver salt, or an acid in a suitable diluent, in which a resulting inorganic salt is insoluble and can thus be removed from the reaction medium. Acid addition salts may also be converted into another acid addition salt by treatment with an anion exchange preparation.

The invention is illustrated in the following non-limiting Examples.

EXAMPLE 1

Tropyl 3,5-Dichlorobenzoate (Formula I, $R_1=R_2=Cl$, $R_3=H$)

Tropine (34.24 g) is treated with anhydrous diethyl ether and ethereal hydrogen chloride and the precipitated hydrochloride is isolated by evaporation of the solvent. 3,5-Dichlorobenzoylchloride (51.7 g) is added and the mixture stirred at 140° C. for 15 minutes during which time the mixture liquifies, evolves hydrogen chloride gas and resolidifies. After heating for a further 15 minutes the cooled solid is dissolved in water, an excess of an aqueous solution of potassium carbonate is added, and the base is extracted with ethyl acetate. Evaporation of the dried ethyl acetate solution yields a solid which is recrystallized from aqueous methanol to yield tropyl 3,5-dichlorobenzoate, m.p. 95° C. (51.8 g).

$C_{15}H_{17}NO_2Cl_2$: Calculated: C, 57.33; H, 5.46; N, 4.46%. Found: C, 57.55; H, 5.53; N, 4.47%.

The following compounds are prepared by the same method: tropyl 3,5-dimethoxybenzoate, m.p. 200° C.; tropyl 3-chlorobenzoate hydrochloride, m.p. 235°–236° C.; tropyl 3,4,5-trimethoxybenzoate, m.p. 118° C.

EXAMPLE 2

Tropyl 3,5-Dimethylbenzoate Hydrochloride (Formula I, $R_1=R_2=CH_3$, $R_3=H$)

A stirred mixture of tropine hydrochloride (5.27 g) and 3,5-dimethylbenzoyl chloride (5 g) is heated at 130°–140° C. for 30 minutes during which time the mixture liquifies, evolves hydrogen chloride gas and resolidifies. A solution of the cooled solid in water is basified with a solution of potassium carbonate and the base extracted with ethyl acetate. The ethyl acetate solution is washed several times with water, dried over mangnesium sulphate, and evaporated to yield the free base which is converted to the hydrochloride by the addition of ethereal hydrogen chloride. Recrystallization of the precipitated solid from ethanol yields tropyl 3,5-dimethylbenzoate hydrochloride (5.4 g) m.p. 260° C.

$C_{17}H_{24}NO_2Cl$: Calculated: C, 65.88; H, 7.75; N, 4.52%. Found: C, 65.92; H, 7.67; N, 4.34%.

EXAMPLE 3

Tropyl 3-Chloro-5-Methylbenzoate (Formula I, $R_1=Cl$, $R_2=CH_3$, $R_3=H$)

5-Chloro-m-xylene

A solution of 3,5-dimethylaniline (36.3 g; 0.3 mole) in glacial acetic acid (200 ml) is treated with methanesulfonic acid (60 g) and the stirred mixture cooled to 0°–5° C. in an ice-salt bath. An ice cold solution of sodium nitrite (21 g in 80 ml H₂O) is slowly added over a half hour period and this diazonium solution then added quickly to an ice cold solution of cuprous chloride [from cooper sulphate 5 H₂O (125 g), sodium chloride (32.5 g) and sodium sulphate (71 g)] in concentrated hydrochloric acid (160 ml). The mixture becomes very thick and is allowed to warm to room temperature. The stirring is continued overnight and the solution heated to 60° C. for ½ hour. Concentrated ammonia is added with cooling until the solution is alkaline and the oil extracted with ether. Distillation of the dried ether extract gives 5-chloro-m-xylene, b.p. 70°–73°/12 mm (25.6 g).

3-Chloro-5-methylbenzoic acid

A well stirred mixture of N-bromosuccinimide (32.5 g), 5-chloro-m-xylene (25.6 g) and carbon tetrachloride (500 ml) is refluxed for 8 hours. The solution is well illuminated and every 2 hours small quantities of benzoyl peroxide are added. The cooled mixture is filtered and the solvent evaporated to give an oil consisting of a mixture of 3-chloro-5-methylbenzyl bromide and 5-chloro-m-xylene in a ratio of about 2:1 (34.5 g).

The above mixture is added to a stirred mixture of potassium tert-butoxide (14 g), 2-nitropropane (11 g)

and dimethylsulphoxide (100 ml) and the mixture is stirred overnight at room temperature. Water (500 ml) is added and the separated oil extracted with ether. Evaporation of the dried ether solution yields an oil consisting of a mixture of 3-chloro-5-methyl-benzaldehyde and 5-chloro-m-xylene (approximately 1:1) (18.5 g).

The above mixture is slowly added over a 15 minute period to a stirred suspension of moist silver oxide [prepared from silver nitrate (24 g) and an aqueous solution of sodium hydroxide (5.7 g)] in a solution of sodium hydroxide (5.7 g) in water (50 ml). The stirred mixture is refluxed for 30 minutes, cooled, filtered and the filtrate extracted with ether. Acidification of the aqueous layer with 2N HCl yields a precipitate which is filtered and recrystallized from aqueous methanol to yield 3-chloro-5-methylbenzoic acid, 174°–175° C. (9.4 g).

Tropyl 3-chloro-5-methylbenzoate

A mixture of 3-chloro-5-methylbenzoic acid (9.4 g) and phosphorous pentachloride (11.6 g) is stirred at room temperature for 1 hour and then distilled to yield phosphorous oxychloride, b.p. 45°/85 mm and 3-chloro-5-methylbenzoyl chloride, b.p. 56°/0.1 mm (10 g).

Tropine (7.4 g) is treated with anhydrous diethyl ether and ethereal hydrogen chloride and the precipitated hydrochloride is isolated by evaporation of the solvent. 3-Chloro-5-methylbenzoyl chloride (10 g) is added and the mixture is stirred at 140°–160° C. for 45 minutes. The cooled mixture is dissolved in water, an excess of an aqueous solution of potassium carbonate added and the base extracted with ethyl acetate. Evaporation of the ethyl acetate yields a residue (10.5 g) which is treated with a solution of methanesulphonic acid (3.43 g) in ethanol (50 ml). The solution is concentrated and cooled to yield crystals of tropyl 3-chloro-5-methylbenzoate methanesulphonate, mp 185° C. (10.9 g).

$C_{17}H_{24}NO_5ClS$: Calculated: C, 52.37; H, 6.20; N, 3.59. Found: C, 52.36; H, 6.15; N, 3.57.

EXAMPLE 4

Tropyl 3,4,5-Trimethylbenzoate (Formula I, $R_1=R_2=R_3=CH_3$)

A mixture of 3,4,5-trimethylbenzoic acid (prepared according to Ber. 27, 3444, 1984) (0.9 g) and phosphorus pentachloride (1.15 g) is stirred at room temperature for 1 hour and the phosphorus oxychloride evaporated under reduced pressure. The oily residue of 3,4,5-trimethylbenzoyl chloride is stirred with the hydrochloride of tropine (from 0.8 g of tropine) at 130°–140° C. for ½ hour. The cooled solid residue is dissolved in water, the solution made alkaline by the addition of potassium carbonate solution and extracted with ether. The ether extract is washed several times with water before being evaporated to dryness. The addition of ethereal hydrogen chloride to the residue provides a solid hydrochloride which is recrystallized from isopropanol to yield tropyl 3,4,5-trimethylbenzoate hydrochloride m.p. 297° (350 g).

$C_{18}H_{26}NO_2Cl$: Calculated: C, 66.79; H, 8.10; N, 4.33%. Found: C, 66.94; H, 7.91; N, 4.34%.

EXAMPLE 5

Antagonism of the Von Bezold-Jarisch reflex evoked by 5-HT in the anaesthetized rat was measured for tropyl 3,5-dimethoxybenzoate (A), tropyl 3,5-dimethylbenzoate (B) and tropyl 3,5-dichlorobenzoate (C) using the following method.

Male Sprague-Dawley rats weighing 250–300 g are anaesthetized with urethane, 1.25 g/kg injected intraperitoneally and set up for recording blood pressure and heart rate as described in J. R. Fozard et al, J. Cardiovas. Pharmacol. 2, 229–245 (1980). A submaximal dose of 5-HT (2 g/kg) is given repeatedly into the cannulated jugular vein and changes in heart rate are quantified. Antagonists are given intravenously and the doses required to just inhibit the response to 5-HT (threshold dose) or to inhibit the response to 5-HT by 50% ($ED_{50}$) are determined.

The results obtained are set forth in Table IV below in which the compounds are identified by the reference letters used above.

TABLE IV

| | VON BEZOLD-JARISCH REFLEX ANTAGONISM | |
|---|---|---|
| COMPOUND | THRESHOLD DOSE (μg/kg) | $ED_{50}$ (μg/kg) |
| A | 6.96 ± 0.90 | 13.7 ± 1.20 |
| B | 3.57 ± 0.33 | 6.07 ± 0.72 |
| C | 7.72 ± 0.63 | 22.0 ± 3.2 |

In a comparative test, metoclopramide gave a threshold dose of 233.4±66.3 μg/kg and an $ED_{50}$ of 408.4±80.9 μg/kg.

This comparative test shows that compounds A, B and C are many times more potent than metoclopramide in this particular test indicating a corresponding reduction in dosage levels in the treatment of migraine.

Compounds A, B and C are also relatively non-toxic as shown their respective $LD_{50}$ values in the mouse and rat (see Table V).

TABLE V

| | $LD_{50}$ IN THE MOUSE AND RAT | | | | | |
|---|---|---|---|---|---|---|
| | MOUSE (mg/kg) | | | RAT (mg/kg) | | |
| ROUTE | A | B | C | A | B | C |
| i.p. | 28 | 47 | 32 | NT | NT | NT |
| s.c. | 17 | NT | NT | NT | NT | NT |
| i.v. | 29 | 17 | 24 | 13 | 9 | 14 |
| oral | 160 | 116 | 90 | NT | NT | NT |

(NT: Not tested)

EXAMPLE 6

Selectivity of Action

A selection of classical in vitro pharmacological test preparations (rat uterus, rat fundus, guinea-pig ileum, guinea-pig *taenia caeci*) were set up according to well-established procedures (see "Pharmacological Experiments on Isolated Preparations" Staff of the Department of Pharmacology, University of Edinburgh, Livingstone, Edinburgh 1970). Various spasmogens were used to elicit contraction of these tissues though mechanisms other than the 5-HT "M" receptor. The concentrations of tropyl 3,5-dimethoxybenzoate (A), tropyl 3,5-dimethylbenzoate (B) and tropyl 3,5-dichlorobenzoate (C) which reduced the effects of a submaximal dose of agonist by 50% were determined ($IC_{50}$). The results are set forth in Table VI below in which the compounds are identified by the reference letters used above.

From Table VI it is clear that A, B and C were at least 700 times and in several instances greater than 50,000 times more potent as blockers of the 5-HT M receptor than of responses elicited through other means.

intolerance. Cumulative doses as high as 177 mg over 18 days were also well tolerated.

TABLE VI

| | CONCENTRATION IN NM TO INHIBIT STANDARD RESPONSE TO STIMULANTS BY 50% | | | | | | | | | | | | |
|---|---|---|---|---|---|---|---|---|---|---|---|---|---|
| | RABBIT HEART | | | RAT UTERUS | | RAT FUNDUS | | GUINEA-PIG ILEUM | | | GUINEA-PIG TAENIA CAECI* | | |
| AGONIST | A | B | C | A | C | A | C | A | B | C | A | B | C |
| 5-HT | 9.4 | 1.03 | 0.82 | >52480 | 25440 | 40016 | >50880 | | | | | | |
| OXYTOCIN | | | | >52480 | >50880 | | | | | | | | |
| ACETYLCHOLINE | | | | | | 13120 | 12402 | 9565 | 9590** | 8055 | | | |
| HISTAMINE | | | | | | | | 6613 | NT | 3676 | | | |
| CALCIUM | | | | | | | | | | | 36080 | 34230 | 28620 |

*In potassium-depolarized Tyrode solution
**Carbachol agonist instead of acetylcholine
NT Not tested

EXAMPLE 7

Pilot Study of Tolerance to Intravenous Tropyl 3,5-Dichlorobenzoate in Patients with Migraine or Cluster Headaches This study was designed to evaluate tolerance and, if possible, efficacy of intravenous tropyl 3,5-dichlorobenzoate in patients with migraine or cluster headaches.

Eight patients (4 males), aged 27–47 with known headache disorders of 5–27 years duration (see Table VII) took part in the study but Patients Nos. 2 and 4 had cluster not migraine headaches and the cause of headaches in Patient No. 6 was unknown.

Tropyl 3,5-dichlorobenzoate was provided as a sterile solution, 1 mg/ml; the desired dose to be diluted in 10 ml normal saline for intravenous infusion over a 2 minute period. No other therapy was taken for at least 24 hours before treatment or during the course of therapy.

The initial dose of 1 mg, when shown to be well tolerated, was increased gradually in subsequent patients (Table VIII). Doses as high as 14 mg/day and 9 mg single dose were administered without any signs of In two of the three patients treated with repeated doses of tropyl 3,5-dichlorobenzoate (Patients Nos. 6 and 8), a marked diminution of headache and associated symptoms occurred. Thus, Patient No. 6, refractory to standard migraine therapies, had a slight reduction in her bilateral headache with 3 mg single doses and a further amelioration with 4 mg bid. This reduction in headache intensity lasted over a 2½ week period. Patient No. 8, an abuser of analgesics with daily bilateral headaches accompanied by nausea, vomiting, vertigo and photophobia, had a decrease in all symptoms with the first dose of 3 mg. This amelioration continued with subsequent increases in doses, except for a single episode of symptom return on first day of 9 mg. Within 6–7 days of stopping therapy, headaches returned to pretreatment intensity.

It can be seen from Table VIII that single intravenous doses of tropyl 3,5-dichlorobenzoate up to 9 mg or repeated doses up to 7 mg b.i.d were well tolerated in patients with headaches. In some patients treated with doses of 3 mg or greater, pain intensity and associated symptoms were ameliorated.

TABLE VII

| PATIENT CHARACTERISTICS | | | | | | | |
|---|---|---|---|---|---|---|---|
| PATIENT | SEX | AGE | WEIGHT | TYPE OF HEADACHE | HISTORY OF HEADACHE | USUAL FREQ. | USUAL DURATION |
| 1 | M | 45 | 65 | Chronic with exacerbations | 19 years | 2–3/week | 18–24 hours |
| 2 | M | 27 | 70 | Cluster | 5 years | daily | 30–45 minutes |
| 3 | F | 31 | 67.4 | Continuous with exacerbations | 10 years | daily | continuous |
| 4 | M | 47 | 66 | Cluster | 11 years | 2–3/day | 1–2 hours |
| 5 | M | 43 | 84.7 | Chronic with daily crises, "Hortonlike" | 20 years | daily | 3–4 hours |
| 6 | F | 45 | 74 | ? | 27 years | daily | ? |
| 7 | F | 34 | 53 | Continuous with exacerbations, and extracranial pain | 11 years | 3–4/week | 3–5 hours |
| 8 | F | 36 | 51.2 | Chronic with daily exacerbations | 7 years | daily | 4–6 hours |

TABLE VIII

| TREATMENT AND RESPONSE | | | |
|---|---|---|---|
| PATIENT | POSOLOGY (intravenous) | RESPONSE | TOLERANCE |
| 1 | 1 mg, then 1 hour later, 2 mg | no effect on headache or nausea | good |
| 2 | 1 mg | no effect | good |
| 3 | 3 mg | no effect | good |
| 4 | 3 mg | no effect | good |
| 5 | 5 mg | no effect | good |
| 6 | 3 mg, single doses × 3 days, then 4 mg bid × 2 days, then | reduction of pain intensity by 70–80% within 30 minutes after 4 mg dose and | good |

TABLE VIII-continued

| | TREATMENT AND RESPONSE | | |
|---|---|---|---|
| PATIENT | POSOLOGY (intravenous) | RESPONSE | TOLERANCE |
| 7 | 5 mg bid × 2 days, then 6 mg bid × 11 days | lasting 4–8 hours; no greater effect with increased doses | |
| | 3 mg × 1 day, then 5 mg × 2 days then 7 mg × 1 day | no effect | good |
| 8 | 3 mg × 2 days, then 6 mg × 1 day 7 mg × 2 days and 9 mg × 1 day | reduction of pain by about 30% with 3 mg, and maintained during increasing doses except for single episode of pain, nausea, vomiting and photophobia on first day of 9 mg | good |

In the following Examples relating to pharmaceutical compositions, the term "active compound" is used to indicate the compound tropyl 3,5-dichlorobenzoate. This particular compound may be replaced in these compositions by any other compound of formula (II), for example, by tropyl 3,5-dimethylbenzoate or tropyl 3-chloro-5-methylbenzoate. Adjustments in the amount of medicament may be necessary or desirable depending upon the degree of activity of the medicament, as is well known in the art.

EXAMPLE 8

An illustrative composition for hard gelatin capsules is as follows:
(a) active compound 5 mg
(b) talc 5 mg
(c) lactose 90 mg The formula is prepared by passing the dry powders of (a) and (b) through a fine mesh screen and mixing them well. The powder is then filled into hard gelatin capsules at a net fill of 100 mg per capsule.

EXAMPLE 9

An illustrative composition for tablets is as follows:
(a) active compound 5 mg
(b) starch 43 mg
(c) lactose 50 mg
(d) magnesium stearate 2 mg The granulation obtained upon mixing the lactose with the compound (a) and part of the starch and granulated with starch paste is dried, screened and mixed with the magnesium stearate. The mixture is compressed into tablets weighing 100 mg each.

EXAMPLE 10

An illustrative composition for an injectable suspension is the following 1 ml ampul for an intramuscular injection:

| | | Weight percent |
|---|---|---|
| (a) | active compound | 0.01 |
| (b) | polyvinylpyrrolidone | 0.5 |
| (c) | lecithin | 0.25 |
| (d) | water for injection to make | 100.0 |

The materials (a)–(d) are mixed, homogenized and filled into 1 ml ampuls which are sealed and autoclaved 20 minutes at 121° C. Each ampul contains 1.0 mg per ml of compound (a).

EXAMPLE 11

| | | mg/suppository |
|---|---|---|
| (a) | Active compound | 5 |
| (b) | Oil of Theobroma (cocoa butter) | 995 |

The medicament is powdered and passed through a B.S. No. 100 Sieve and triturated with molten oil of Theobroma at 45° C. to form a smooth suspension. The mixture is well stirred and poured into moulds each of nominal 1G capacity, to produce suppositories.

We claim:

1. A method of treating migraine which comprises administering to a patient suffering migraine, an effective migraine relieving amount of a substituted tropyl benzoate having the formula:

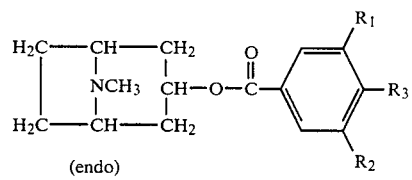

(endo)

wherein
$R_1$ represents $C_1$–$C_4$ alkyl, $C_1$–$C_4$ alkoxy or halogen;
$R_2$ represents hydrogen, $C_1$–$C_4$ alkyl, $C_1$–$C_4$ alkoxy or halogen;
$R_3$ represents hydrogen, $C_1$–$C_4$ alkyl, $C_1$–$C_4$ alkoxy or halogen; provided that $R_3$ is hydrogen when $R_2$ is hydrogen, or a pharmaceutically acceptable salt thereof.

2. A method of prophylaxis of migraine according to claim 1 wherein the patient is at risk of migraine and the amount of compound is an effective prophylactic amount.

3. The method of claim 1 wherein $R_1$ represents methyl, methoxy or chlorine, and $R_2$ and $R_3$ represent hydrogen.

4. The method of claim 1 wherein $R_1$ and $R_2$ are the same and each represents methyl, methoxy or chlorine, and $R_3$ represents hydrogen.

5. The method of claim 1 wherein $R_1$, $R_2$ and $R_3$ are all the same and each represents methyl, methoxy or chlorine.

6. The method of claim 1 wherein the compound is tropyl-3-methoxybenzoate or a pharmaceutically acceptable salt thereof.

7. The method of claim 1 wherein the compound is tropyl-3-chlorobenzoate or a pharmaceutically acceptable salt thereof.

8. The method of claim 1 wherein the compound is tropyl-3-methylbenzoate or a pharmaceutically acceptable salt thereof.

9. The method of claim 1 wherein said compound is administered in an amount of 0.01 mg/kg to 10 mg/kg body weight.

10. The method of claim 1 wherein said compound is administered in an amount of 0.03 mg/kg to 3.0 mg/kg body weight.

* * * * *

UNITED STATES PATENT AND TRADEMARK OFFICE
CERTIFICATE OF CORRECTION

PATENT NO. : 4,563,465

DATED : January 7, 1986

INVENTOR(S) : J. Richard Fozard, et al.

It is certified that error appears in the above-identified patent and that said Letters Patent is hereby corrected as shown below:

At Column 1, line 68, the patent reads "3,4 or 3,4 or" and should read --3,4 or 3,5 or--.

At Column 4, line 30, the patent reads "31-methylbenzoate" and should read --3-methylbenzoate--.

Signed and Sealed this

Twelfth Day of June, 1990

Attest:

HARRY F. MANBECK, JR.

*Attesting Officer*     *Commissioner of Patents and Trademarks*